US006946125B2

(12) United States Patent
Rahal

(10) Patent No.: US 6,946,125 B2
(45) Date of Patent: Sep. 20, 2005

(54) METHODS OF TREATING WEST NILE VIRUS INFECTION

(75) Inventor: James J. Rahal, New York, NY (US)

(73) Assignee: The New York Hospital Medical Center of Queens, Flushing, NY (US)

( * ) Notice: Subject to any disclaimer, the term of this patent is extended or adjusted under 35 U.S.C. 154(b) by 168 days.

(21) Appl. No.: 09/935,966

(22) Filed: Aug. 23, 2001

(65) Prior Publication Data

US 2002/0061290 A1 May 23, 2002

Related U.S. Application Data

(60) Provisional application No. 60/227,422, filed on Aug. 23, 2000.

(51) Int. Cl.[7] .......... A61K 49/00
(52) U.S. Cl. .......... 424/85.4; 435/5
(58) Field of Search .......... 424/85.2, 85.4; 435/5

(56) References Cited

U.S. PATENT DOCUMENTS 6,387,365 B1 * 5/2002 Albrecht et al. .......... 424/85.4

FOREIGN PATENT DOCUMENTS

WO WO 96/36351 11/1996

OTHER PUBLICATIONS

Merimsky et al. Neurotoxicity of interferon–alpha. Anticancer Drugs (1992) vol. 3, No. 6, 567–570.*

Gokcil et al. Alpha–interferon and isoprinosine in adult–onset subacute sclerosing panencephalitis. Journal of Neurological Science (1999) vol. 162, No. 1, pp. 62–64.*

Takahashi et al. The cooperative effect of interferon–alpha and ribavirin on subacute sclerosing panencephalitis (SSPE) virus infections, in vitro and in vivo. Antiviral Research (1998) vol. 37, No. 1, pp. 29–35.*

Crance et al. Antiviral substances inhibiting in vitro replication of several arboviruses (Bunyaviridae, Flaviviridae, Togaviridae. Travaux Scientifiques des Chercheurs du Service de Sante des Armees (1996) vol. 0, No. 17, pp. 57–58. (abstract only).*

Crance et al. Selection of antiviral compounds active on several Flaviviruses: Clinical perspectives.

Travaux Scientifiques des Chercheurs du Service de Sante des Armees. vol. No. 20, pp. 35–36 (1999) and English translation thereof.

Leyseen et al., "Perspectives for the Treatment of Infections with Flaviviridac", Clinical Microbiology Reviews, vol. No. 13, No. 1, pp. 67–82 (2000).

Written Opinion for PCT/US01/26301.

International Search Report for PCT/US01/26301.

Enserink, "West Nile Drugs, Vaccine Still Years Away", Science vol. No. 290 No. 5496, p. 1483 (2000).

Hirsch et al., Nucleoside derivatives and interferons as antiviral agents, Current Clinical Topics in Infectious Disease., vol. 3:30–53 (1981).

Roberts et al., Phase I Clinical Studies of Ribavirin in High Risk Patients for the Acquired Immunodeficiency Syndrome, Academic. Press p. 95–112.

Holmes et al., Lassa Fever in the United States, The New England Journal of Medicine, pp. 1120–1123 (1990).

Odelola, Herbert, Antiviral Activity of Virazole on Replication of Viruses Isolated in Nigeria, Virology, pp. 334–335 (1977).

Update: West Nile Virus Encephalitis–New York, 1999, MMWR 48:944–955.

Guidelines for Surveillance, Prevention, and Control of West Nile Virus Infection–United States, MMWR, 49:2 p. 25–28 (2000).

Update: West Nile Virus Activity–Northeastern United States, MMWR, 49:31 p. 714–718 (2000).

Human West Nile Virus Surveillance–Connecticut, New Jersey, and New York, MMWR, 50:14 p. 265–268 (2000).

Laskin et al., Ribavirin Disposition in High Risk Patients for Acquired Immunodeficiency Syndrome, Clinical Pharmacology And Therapeutics, vol. 41, No. 5 pp. 546–555 (1987).

Roberts et al., Ribavirin Pharmacodynamics in High–Risk Patients for Acquired Immunodeficiency Syndrome, Clinical Pharmacology and Therapeutics, vol. 42, No. 4 pp. 365–373 (1987).

Hosoya et al., High–Dose Intravenous Ribavirin Therapy for Subacute Sclerosing Panencephalitis, Antimicrobial Agents and Chemotherapy, vol. 45, No. 3 pp. 943–945 (2001).

Briese et al., Testing for West Nile Virus, The Lancet, vol. 356:1110 (2000).

Wang et al., Effect of Dosing Selection on Pharmocokinetics of Alpha Interferon and Anti–Alpha Interferon Neutralizing Antibody in Mice, Chronopharmacology of IFN–a, vol. 45:176–180 (2001).

Barry et al., Arenavirus Infection–Connecticut, MMWR, vol. 43 No. 34 pp. 635–636 (1994).

Forni et al., Severe Measles Pneumonitis in Adults: Evaluation of Clinical Characteristics and Therapy with Intravenous Ribavirin, Clinical Infectious Diseases, Vo. 19:454–462 (1994).

Hoch et al., Crimean Congo–Haemorrhagic Fever treated with oral ribavirin, The Lancet, vol. 346:472–476 (1995).

Barry et al., Brief Report: Treatment of a Laboratory–Acquired Sabia Virus Infection, The New England Journal of Medicine, vol. 333:294–318 (1995).

(Continued)

*Primary Examiner*—Ulrike Winkler
(74) *Attorney, Agent, or Firm*—William D. Schmidt; Kalow & Springut LLP

(57) ABSTRACT

The present invention provides methods of preventing or treating West Nile virus as well as infections caused by other viruses of the Flaviviridae family in animals comprising administering to the animal an effective amount of ribavirin and/or interferon alpha-2b.

21 Claims, 2 Drawing Sheets

OTHER PUBLICATIONS

Merigan, Thomas C., Interferon–The First Quarter Century, JAMA, vol. 248 No. 19 pp. 2513–2516 (1982).
Hayden, Fred, Basic Principles in the Diagnosis and Management of Infectious Diseases, Chapter 36 pp. 474–479 (2000).
Smith et al., Distribution of alpha interferon in serum and cerebrospinal fluid after systematic administration, Clin. Pharm. Ther., 37(1):85–88 (1985), Abstract only.
Centers for Disease Control and Prevention. Update: West Nile Virus Activity–Northeastern U.S., MMWR, vol. 284 No. 10 1236–1238 (2000).
Centers for Disease Control and Prevention. Surveillance for West Nile Virus in Overwintering Mosquitoes–New York, vol. 238 No. 18 pp. 2380–2382 (2000).
Centers for Disease Control and Prevention. Update: West Nile Virus Activity–Northeastern United States, vol. 284 No. 13 pp. 1643–1644 (2000).
Centers for Disease Control and Prevention. Update: West Nile Virus Activity–Eastern U.S., vol. 284 No. 24 pp. 3119–3120 (2000).
Briese et al., Detection of West Nile virus sequences in cerebrospinal fluid, The Lancet, vol. 355:1614–1616 (2000).
Briese et al., Identification of a Kunjin/West Nile–like flavivirus in brains of patients with New York encephalitis, The Lancet, vol. 354:1261–1262 (1999).
Kesson et al., Progressive Vaccinia Treated with Ribavirin and Vaccinia Immune Globulin, Clinical Infectious Disease, vol. 25:911–914 (1997).
Ljungman et al., Oral Ribavirin for Prevention of Severe Liver Disease Caused by Hepatitis C Virus During Allogeneic Bone Marrow Transplantation, Clinical Infectious Disease, vol. 23:167–169 (1996).
Japour et al., A Phase–I Study of the Safety, Pharmacokinetics, and Antiviral Activity of Combination Didanosine and Ribavirin in Patients with HIV–1 Disease, Journal of Acquired Immune Deficiency Syndromes and Human Retrovirology, 13:235–246 (1996).
Huggins et al., Prospective, Double–Blind, Concurrent, Placebo–Controlled Clinical Trial of Intravenous Ribavirin Therapy of Hemorrhagic Fever with Renal Syndrome, The Journal of Infectious Disease, vol. 164:1119–1127 (1991).
Paul Glue, M.D., The Clinical Pharmacology of Ribavirin, Seminars in Liver Disease, 19:17–24 (1999).
N. Raphael Shulman, Assessment of Hematologic Effects of Ribavirin in Humans, Academic Press., 94:29251–29264 (1984).
Centers for Disease Control and Prevention. West Nile Virus Activity–New York and New Jersey, vol. 284 No. 7 pp. 823–824 (2000).
Sidwell, R.W. et al., Ribavirin: An antiviral Agent, Pharmacol. Ther., vol. 6 pp. 2928529308, (1979).
Phochoda et al., Hantavirus–Associated Acute Respiratory Failure, The New England Journal of Medicine, pp. 1744 (1993).
Centers for Disease Control and Prevention. Guidelines for Surveillance, Prevention, and Control of West Nile Virus Infection–U.S. vol. 49 No. 2 pp. 25–28 (2000).
Holmes et al., Lassa Fever in the United States, The New England Journal of Medicine, 323:11201123 (1990).
Cardiovascular Infection by Chlamydia pneumonia Is Not Related to Apolipoprotein E Genotype, Clinic of Infectious Disease 2000;31:1515–1516.
Ishii et al., Effective Ribavirin Concentration in Hamster Brains for Antiviral Chemotherapy for Subactue Sclerosing Panencephalitis, Antimicrobial Agents and Chemotherapy, vol. 40 No. 1 pp. 241–243 (1996).
Sidwell, R.W., Ribavirin: In Vitro Antiviral Activity, Academ. Press., vol. 94 pp. 29265–29284 (1980).
Maslo et al., Ribavirin Therapy for Adenovirus Pneumonia in an AIDS Patient, Amer. Journal Respir. Crit. Care Med., vol. 156:1263–1264 (1997).
Lewisohn et al., Phase I Study of Intravenous Ribavirin Treatment of Respiratory Syncytial Virus Pneumonia after Marrow Transplantation, Antimicrobial Agents and Chemotherapy, vol. 40 No. 11 p. 2555–2557 (1996).
CID: Reassessment of the Indications for Ribavirin Therapy in Respiratory Syncytial Virus Infections, Pediatrics vol. 97 No. 1 pp. 137–140 (1996).
Bisceglie et al., Ribavirin as Therapy for Chronic Hepatitis C, American College of Physicians, vol. 123 No. 12 p. 897–902 (1995).
The Ribavirin ARC Study Group, Multicenter Clinical Trial of Oral Ribavirin in Symptomatic HIV–Infected Patients, Journal of Acquired Immune Deficiency Syndrome, vol. 6 No. 1 pp. 32–41 (1993).
Going et al., Ribavirin for Syncytial Giant Cell Hepatitis, The Lancet, vol. 341 p. 640 (1993).
Isaacs, D., Ribavirin, Pediatrics, vol. 79 No. 2 pp. 289–291 (1987).
Prows, C.A., Ribavirn's Risks in Reproduction–How Great Are They?, MCN, vol. 14:400–404 (1989).
Centers for Disease Control and Prevention. Human West Nile Virus Surveillance–Connecticut, New Jersey, an New York, vol. 285 No. 17 pp. 2188–2190 (2001).
Canonico et al., Effects of Ribavirin on Red Blood Cells, Toxicology and Applied Pharmacology, vol. 74 p. 155–162 (1984).
Lanciotti, et al., Origin of the West Nile Virus Responsible for an Outbreak of Encephalitis in the Northeastern United States, Science, vol. 286 pp. 2333–2338 (1999).
Jia et al., Genetic analysis of West Nile New York 1999 encephalitis virus, The Lancet, vol. 354 p. 1971–1972 (1999).
Monath et al., Flaviviruses, Clinical Virology, vol. 49:1133–1140.
Bisceglie, A.M., Hepatitis C, The Lancet, vol. 351 p. 351–356 (1998).
Hubalek et al., West Nile Fever–a Reemerging Mosquito–Borne Viral Disease in Europe, Emerging Infectius Diseases, vol. 5 No. 5 pp. 643–650 (1999).
The City of New York Department of Health, Alert: Preliminary Results from the Oct. 1999 Serosurvey for West Nile Virus in Northern Queens, (2000).
Update: West Nile Virus Encephalitis–New York, 1999, MMWR, vol. 48 No. 41 pp. 944–947 (1999).
Quagliarello, V., Emergence of West Nile Virus Encephalitis in the New York Metropolitan Area, Clinical Infectious Disease vol. 2 pp. 325–326 (2000).
Chen, David W., Lives that have been changed forever from after effects of a mosquito bite, The New York Times, pB1, Aug. 19, 2000.
Klein et al., West Nile Virus in Nassau County, New York: The Long Island Experience, Infectious Disease in Clinical Practice, vol. 9 No. 7 pp. 303–308 (1999).

Shieh et al., The Role of Pathology in an Investigation of an Outbreak of West Nile Encephalitis in New York, Emerging Infectious Diseases, vol. 6 No. 4 pp. 370–372 (2000).

Sampson BA, The pathology of human West Nile Virus Infection, Hum Pathol, vol. 31(5) pp. 527–531 (2000), Abstract only.

Nichter et al., Rhombenecephalitis caused by West Nile fever virus, Neurology, Jul. (1 of 2) 2000 p. 153.

Asnis et al., The West Nile Virus Outbreak of 1999 in New York: The Flushing Hosptal Experience, Clinical Infectious Diseases, 30:413–418 (2000).

Ahmed et al., Guillain–Barre syndrome: An unusual presentation of West Nile virus infection, Neurology, pp. 144–146 (2000).

Silak et al., West Nile Viral Encephalitis in an HIV–Positive Woman in New York, The New England Journal of Medicine, vol. 342 No. 1 pp. 59–60 (2000).

Tsai et al., West Nile Encephalitis epidemic in southeastern Romania, The Lancet, vol. 352 pp. 767–771 (1998).

Han et al., Risk Factors for West Nile Virus Infection and Meningoencephalitis, Romania, 1996, The Journal of Infectious Diseases, vol. 179 pp. 230–233 (1999).

Glue, Paul, The Clinical Pharmacology of Ribavirin, Seminars in Liver Disease, vol. 19 pp. 17–24 (1999).

Anderson et al., Isolation of West Nile Virus from Mosquitoes, Crows, and a Cooper's Hawk in Connecticut, Science, vol. 286 pp. 2331–2333 (1999).

McCormick et al., Effective Therapy with Ribavirin, The New England Journal of Medicine, vol. 314 No. 1 pp. 20–26 (1998).

Jordan et al., Ribavirin Inhibits West Nile Virus Replication and Cytopathis Effect in Neural Cells, The Journal of Infectious Diseases, vol. 182 pp. 1214–1217 (2000).

Forni, et al., Severe Measles Pneumonitis in Adults: Evaluation of Clinical Characteristics and Therapy with Intravenous Ribavirin, Clinical Infectius Diseases, vol. 19 pp. 454–462 (1994).

Jacobsen, et al., Psychological Reactions of Individuals at Risk for AIDS During an Experimental Drug Trial, Psychosomatics, vol. 29 No. 2 (1988).

Roberts et al., A Phase I Study of Ribavirin in Human Immunodeficiency Virus–Infected Patients, The Journal of Infectious Diseases, vol. 162 pp. 638–642 (1990).

The Ribavirin ARC Study Group, Multicenter Clinical Trial of Oral Ribavirin in Symptomatic HIV–Infected Patients, Journal of Acquired Immune Deficiency Syndromes, vol. 6 pp. 32–41 (1993).

Budsworth et al., Ribavirin: A Role in HIV Infection?, Journal of Acquired Immune Deficiency Syndromes, vol. 3 pp. 893–895 (1990).

Budsworth et al., Letters to the Editor, Journal of Acquired Immune Deficiency Syndromes, vol. 3 pp. 1017–1021 (1990).

Roberts et al., A Multicenter Clinical Trial of Oral Ribavirin in HIV–Infected Patients with Lymphadenopathy, Journal of Acquired Immune Deficiency Syndromes, vol. 3 pp. 884–892 (1990).

MMWR Update: West Nile Virus Isolated from Mosquitoes–New York 2000, vol. 49 No. 10.

MMWR Update: Surveillance for West Nile Virus in Overwintering Mosquitoes–New York 2000, vol. 49, No. 9 p. 178–179.

Khakoo, S. ,J. Clin Pharmacol, vol. 46, p. 563–570.

Wall Street Journal, ICN Drug is Found Useful in Treating Hepatisis C, May 3, 1991.

Roberts, Richard, Abstract Form: In Vitro Activity of Ribavirin in Acute and Cocultivated HIV Infection of Human Peripheral Blood Mononuclear Cells, International Conference on Aids, Montreal Jun. 4–9, 1989.

Reuters Information Service, Inc., ICN Says Ribavirin in Study Encouraging, Chicago–Oct. 1, 1993.

Hepatitis C Virus, Hepatitis Viruses Chapter 62 p. 533.

Antiviral Activity of Interferons, Interferons p. 393–410 chapter 16.

Arthropod–Borne Group B Virus Infections of Man, West Nile Fever p. 321–324.

* cited by examiner

Figure 1. α-IFN 1.5 hr post-infection
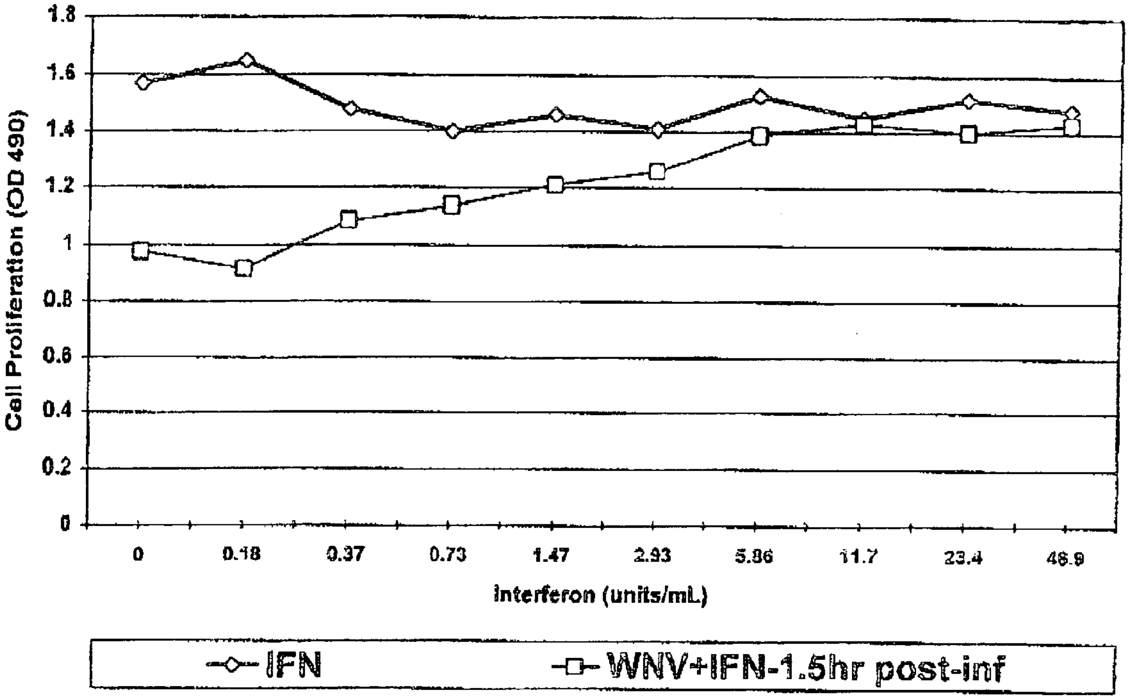

Figure 2. α-IFN (0.37 units/mL) + RV (dilutions)
1.5 hr post-infection
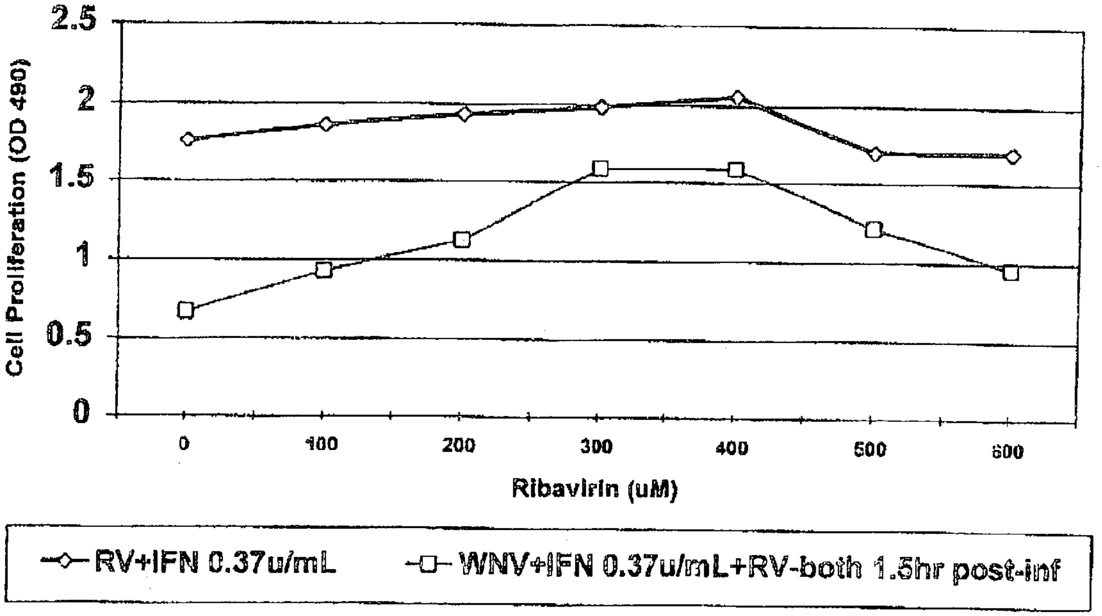

METHODS OF TREATING WEST NILE VIRUS INFECTION

This application claims the benefit of the filing date of Provisional Application No. 60/227,422, filed Aug. 23, 2000, entitled "Methods for Treating West Nile Virus" this entire disclosure is hereby incorporated by reference into the present disclosure.

BACKGROUND

West Nile virus an arthropod-borne flavivirus, has emerged in recent years as a deadly health threat to not only humans, but also to other animal species such as horses and birds. New York was the first area in North American to report cases of West Nile virus infections.

West Nile virus infection in humans has been found previously only in Africa, the Middle East and Eastern Europe. The virus is transmitted to humans and several animal species by mosquitoes which acquire the virus by feeding on infected birds. It is not known how West Nile virus was transmitted into the United States, however, scientists believe that it may have been transmitted through immigration or importation of an infected human, bird or mosquito from an endemic area.

Nevertheless, West Nile virus remains a continued threat to public health. Epidemiologic and virologic studies indicate that live virus persists in mosquito and bird populations. Mosquito control measures were implemented in New York, New Jersey and Connecticut, yet new cases of West Nile virus are being diagnosed. Certain populations are still being exposed to West Nile virus. For example, West Nile virus sero-prevalence studies in Queens, N.Y. indicate that 2.6% of the population, age 5 or older, had evidence of prior infection. Thus, a large portion of the population in Queens, and probably a larger portion in surrounding areas, remains susceptible to West Nile virus.

Among infected humans, approximately one in every 150 to 300 become ill with fever, myalgia and possible rash. Among those who are symptomatic, approximately 10–15% will have evidence of meningitis (headache, stiff neck) or encephalitis (change of mental status, peripheral neurologic abnormalities, muscle weakness). Though most humans with meningitis or encephalitis in New York were over age 50, older age was not associated with meningoencephalitis among 393 cases reported in the 1996 Romanian outbreak. However, almost all fatalities have occurred among humans over the age of 50. Underlying preexisting medical conditions were present in several fatal cases in New York, but were not risk factors for meningoencephalitis in Romania. The fatality rate among patients with central nervous system infection was 5% in Romania and 11% in New York. Fatalities have been due to prolonged central nervous system dysfunction requiring ventilatory support and leading to secondary complications. Prolonged neurologic symptoms have occurred in survivors of encephalitis.

Prior to the New York outbreak, fatal infection in birds (i.e. crows) was unusual. The New York strain of West Nile virus is most closely related to an isolated virus from a dead goose in Israel where increased pathogenicity of West Nile virus for birds was also noted.

The diagnosis of acute West Nile virus infection in humans is established by the presence of IgM antibody in serum or cerebrospinal fluid, a four-fold increase in antibody by ELISA or neutralization, or identification of West Nile virus RNA in brain tissue by polymerase chain reaction, or viral isolation. Occasionally, viremia (virus is in blood) occurs, but isolation of West Nile virus from blood has been uncommon.

To date, no effective prevention or treatment of West Nile virus infection exists. Until the present invention, prevention or treatment of West Nile virus infection was merely supportive (i.e. anti-pyretics are given to keep fever down, fluids, antibiotics for secondary bacterial infection, respiratory support as necessary, etc. One author in an abstract described activity of ribavirin against West Nile virus infection in mice. To date, ribavirin has not been used in the prevention or treatment of West Nile virus in humans.

Ribavirin and interferon alpha-2b are active against hepatitis C virus which is a member of the genus Flavivirus. West Nile virus is also a member of the genus Flavivirus. However, to date ribavirin in combination with interferon alpha-2b or interferon alpha-2b has not been used to prevent or treat West Nile virus infection in animals.

Based on the foregoing, there is a need for effective methods of preventing or treating deadly West Nile virus and other infections in humans and animals. Accordingly, there is also a need for effective combination therapy to prevent or treat West Nile virus.

SUMMARY OF THE INVENTION

The present invention provides a method of preventing or treating West Nile virus in a human comprising administering to the human an effective amount of ribavirin.

In one embodiment, the present invention provides a method of preventing or treating West Nile virus in an animal comprising administering to the animal an effective amount of interferon alpha-2b.

In a second embodiment, the present invention provides a method of preventing or treating West Nile virus in an animal comprising administering to the animal an effective amount of ribavirin and interferon alpha-2b.

In a third embodiment, the present invention provides a method for treating or preventing central nervous system infections due to West Nile Virus, or other closely related infections resulting from mosquito-born members of the family Flaviviridae. by administering to the animal an effective amount of ribavirin and/or interferon alpha-2b. These closely related infections include St. Louis encephalitis, Japanese encephalitis, Murray Valley encephalitis (subsequently referred to as WNV).

For a better understanding of the present invention together with other and further advantages and embodiments, reference is made to the following description taken in conjunction with the examples, the scope of which is set forth in the appended claims.

BRIEF DESCRIPTION OF THE FIGURES

Preferred embodiments of the invention have been chosen for purposes of illustration and description, but are not intended in any way to restrict the scope of the invention. The preferred embodiments of certain aspects of the invention are shown in the accompanying figures, wherein:

FIG. 1 illustrates effects of varying concentrations of interferon alpha-2b on WNV infected Vero cells. The vertical axis represents a calorimetric assay of cellular lactic dehydrogenase which is directly proportional to cell viability and proliferation.

FIG. 2 illustrates effects of varying concentrations of ribavirin plus a constant subinhibitory concentration of interferon alpha 2b (0.37 units/ml) on WNV infected Vero cells. The vertical axis represents a colorimetric assay of cellular lactic dehydrogenase which is directly proportional to cell viability and proliferation.

DETAILED DESCRIPTION OF THE INVENTION

The invention has been developed based on the Applicants' unexpected observation that ribavirin and/or interferon alpha-2b therapy is useful for preventing or treating WNV. Applicants are unaware of any prophylactic or treatment regimens that employ ribavirin and/or interferon alpha-2b for treating WNV.

WNV is a pathogenic virus from the family Flaviviridae, within the Japanese Encephalitis Antigenic Complex.

The diagnosis of WNV infection in humans can be established by the presence of WNV IgM antibody in serum or cerebrospinal fluid, increases in WNV antibody detected by ELISA or WNV neutralizing antibody, identification of WNV RNA in tissue by polymerase chain reaction, viral isolation in fluids such as in cerebral spinal fluid and/or blood.

Some medical and veterinary symptoms, syndromes, conditions or diseases associated with WNV include but are not limited to one or more of the following: infection, viremia, stiff neck, headache, fever, myalgia, change of mental status, peripheral neurologic abnormalities, muscle weakness, rash, meningitis, encephalitis and/or meningoencephalitis.

Typically, fatalities result from encephalitis or meningoencephalitis. As used herein meningitis is an art recognized term and includes inflammation of the meninges of the brain. Encephalitis includes inflammation of the brain. Meningoencephalitis is a combination of meningitis and encephalitis and includes inflammation of the spinal cord covering (meninges) and brain.

Some types of encephalitis associated with West Nile Virus include, but are not limited to, St. Louis encephalitis, Japanese encephalitis or Murray Valley encephalitis.

The methods of the present invention includes administering an effective amount of one or more compositions including ribavirin. For purposes of the present invention, ribavirin is a nucleoside analog with antiviral activity. The chemical name of ribavirin is 1-β-D-ribofuranosyl-1H-1,2,4-triazole-3-carboxamide. Ribavirin has the empirical formula $C_8H_{12}N_4O_5$ and the molecular weight is 244.21. Ribavirin is available from various pharmaceutical companies. For example, a ribavirin composition is available as REBETOL® from Schering Plough Corporation, New Jersey.

The present invention also includes pharmaceutically acceptable salts of ribavirin. Some examples of pharmaceutically acceptable salts include those salt-forming acids and bases that do not substantially increase the toxicity of the compound. Some examples of suitable salts include salts of alkali metals such as magnesium, potassium and ammonium. Salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

An effective amount of ribavirin as used herein is that amount effective to achieve the relief or palliation of symptoms, condition and/or diseases associated with WNV. Preferably, ribavirin is administered in an amount that inhibits the growth or replication of the WNV.

The minimal dose of ribavirin for a human is the lowest dose that achieves the desired result. For example, ribavirin is administered at a dose of from about 300 mg to about 3600 mg/day. Preferably, ribavirin is administered in an amount of 1200 mg as an initial dose, then 600 mg every 6 hours for 10 days.

Maximal dose for a human is the highest dosage that does not cause undesirable or intolerable side effects. For example, a maximal dose is a dose lower than 20–200 mg/kg (estimated human equivalent of 1.67–16.7 mg/kg) which is known to be mutagenic in mice. In determining the maximal and minimal dose, the practitioner is guided by skill and knowledge in the field, and the present invention includes without limitation dosages that are effective to achieve the described antiviral effect.

Administering ribavirin can be accomplished in a variety of ways. In cultured cellular or tissue systems, ribavirin can be administered by contacting the cells or tissue directly with an effective amount of ribavirin. In humans, ribavirin can be administered orally or enterally which is the preferred route of delivery. Compositions such as tablets, capsules, pills, troches, elixirs, suspensions, syrups, wafers, chewing is gum and the like can be employed to provide ribavirin.

Ribavirin can also be administered by the parenteral route. For example, ribavirin can be administered intravenously (e.g., intravenous injection). Intravenous administration can be accomplished by mixing ribavirin in a suitable pharmaceutical carrier (vehicle) or excipient as understood by practitioners in the art.

The present invention includes methods of treating WNV in an animal suffering therefrom comprising administering to the animal an effective amount of one or more compositions including interferon alpha-2b. For purposes of the present invention, interferon alpha-2b is a soluble protein composed of 165 amino acids with a molecular weight of 19,271 daltons that exhibits antiviral activity. Interferon alpha-2b is available from various pharmaceutical companies. For example, a composition comprising interferon alpha-2b is available as INTRON A™ from Schering Plough Corporation, New Jersey. It will be understood that other brands can be used.

While the mechanism of antiviral activity of interferon alpha-2b is still unknown, it is believed that the anti-viral activity of interferon is not caused directly by interferon alpha, rather it is caused by proteins that are induced or signaled by interferon. This signaling pathway activates the immune response of the cell.

Interferon alpha-2b inhibited viral replication at a relatively low concentration (5.9 units/mL) when applied after infection of green monkey kidney cells with WNV. Ribavirin suppressed viral replication at a concentration of 500 $\mu$M when applied after infection. A cytotoxic effect of ribavirin occurred at a concentration of 600–1000 $\mu$M. Thus, interferon alpha-2b possesses greater activity in-vitro than ribavirin, with a potentially greater therapeutic ratio in humans. A dose of 3 million units of interferon alpha-2b in humans provides serum levels of 10 units/mL after 8 hours, and daily doses of 3 million units yield serum levels of 20–30 units/mL, which are above the concentration required for in-vitro efficacy against WNV. Although systemic administration of interferon alpha-2b produces low levels in cerebrospinal fluid and brain, beneficial effects against West Nile encephalitis may occur through suppression of viremia and/or enhancement of cell mediated immunity systemically and in the central nervous system.

An effective amount of interferon alpha-2b as used herein is that amount effective to achieve the relief or palliation of symptoms, condition and/or diseases associated with WNV. Preferably, interferon alpha-2b is administered in an amount that indirectly inhibits the growth or replication of the WNV of the virus by mediating the immune response.

The minimal dosage of interferon alpha-2b for a human is the lowest dose which achieves the desired result. For example, interferon alpha-2b is administered at a dose of from about amount from about 1.5 million units to about 10 million units/day. Preferably, interferon alpha-2b is administered in an amount of 3 million units as an initial dose, then 3 million units every 12–24 hours.

Maximal dosage for a human is the highest dosage that does not cause undesirable or intolerable side effects. For example, a maximal dose is a dose lower than 15 and 30 million units/kg (estimated human equivalent of 5 and 10 million nits/kg) which was shown to have abortifacient effects in pregnant rhesus monkeys. However, in determining the maximal and minimal dose, the practitioner is guided by skill and knowledge in the field, and the present invention includes without limitation dosages that are effective to achieve the described antiviral effect.

Administering interferon alpha-2b can be accomplished in a variety of ways. In cultured cellular or tissue systems, interferon alpha-2b can be administered by contacting the cells or tissue directly with an effective amount of interferon alpha-2b. In humans, interferon alpha-2b can be administered by the parenteral route. For example, interferon alpha-2b can be administered intravenously (e.g., intravenous injection, subcutaneously, intradermally, etc). Intravenous administration can be accomplished by mixing interferon alphaL-2b in a suitable pharmaceutical carrier (vehicle) or excipient as understood by practitioners in the art.

The present invention includes methods of treating WNV in an animal suffering therefrom comprising administering to the animal an effective amount of one or more compositions including ribavirin in combination with interferon alpha-2b. For example, combined or coordinated systemic administration of ribavirin and interferon alpha-2b is also contemplated under the invention. Preferred combined systemic administration includes oral administration of ribavirin to humans in amounts from about 300 mg to about 3600 mg/day and parenteral administration of interferon alpha-2b in an amount from about 1.5 million units to about 10 million units/day.

It is believed that combined administration of ribavirin and interferon alpha-2b is additive or synergistic. Further, it appears that combined treatment increases therapeutic efficacy in tissue culture.

The methods of the present invention can be used in vivo, in vitro, and ex vivo, for example, in living animals as well as in cultured tissue, organ or cellular systems. Animals include mammals, for example, humans, as well as pet animals such as dogs and cats, laboratory mammals, such as rats and mice, and farm animals, such as pigs and horses and cows. Animals include poultry such as chickens and turkeys, and other birds such as pigeons and crows.

Tissues, as used herein, are an aggregation of similarly specialized cells that together perform certain special functions. Cultured cellular systems include any cells that can be infected with WNV, such as for example, blood cells, brain or kidney cells.

In vivo practice of the invention permits application in the prevention, relief or palliation of medical and veterinary, syndromes, symptoms, conditions or diseases associated with WNV associated with WNV. In particular, the method provides a means for protecting animals suffering from diseases or other conditions associated with or mediated by WNV. Such conditions or diseases include but are not limited to: infection, viremia, stiff neck headache, fever, myalgia, change of mental status, peripheral neurologic abnormalities, muscle weakness, rash, meningitis, encephalitis and/or meningoencephalitis.

The methods of the present invention are also applicable for prophylaxis or prevention of disease. Thus, an animal can be given dose(s) of ribavirin and/or interferon alpha 2b on a weekly or daily basis to prevent WNV infection. Such dose(s), preferably, is the same or less than that used for treatment. Preferably, the animal is given preventative doses of ribavirin and/or interferon before exposure to WNV. In any event, in determining the preventative dose, the practitioner is guided by skill and knowledge in the field, and the present invention includes without limitation dosages that are effective to prevent WNV infection.

Having now generally described the invention, the same may be more readily understood through the following reference to the following examples, which are provided by way of illustration and are not intended to be limit the present invention unless specified.

EXAMPLES

The examples below describe methods for preventing and treating WNV in vitro and in vivo.

Example 1

In vitro: Studies have been conducted utilized a bovine kidney cell monolayer infected with a strain of WNV isolated from mosquitoes and birds in Connecticut. Cytotoxicity was assayed by measuring the decrease in release of lactate dehydrogenase from infected cells, as compared with uninfected controls. Experiments were conducted with the addition of serial dilutions of ribavirin, interferon alpha-2b, or both, prior to, or after, infection of cells by WNV. The results are shown in Table 1 and FIGS. 1 and 2.

TABLE 1

Suppression of West Nile virus (WNV) in Vero cell culture by ribavirin and interferon alpha-2b.

| Treatment | Dose | Mean* O.D. 490 value | +SD |
|---|---|---|---|
| Interferon (units/ml) applied 2 hours prior to infection of cells with WNV | 6000 | 0.94b | 0.083 |
| | 3000 | 1.02c | 0.102 |
| | 1500 | 1.09c | 0.050 |
| | 750 | 1.05c | 0.118 |
| | 375 | 1.08c | 0.073 |
| | 188 | 1.07c | 0.070 |
| | 0 | 0.71a | 0.058 |
| Interferon (units/ml) applied 2 hours after infection of cells with WNV | 375.0 | 1.51a | 0.156 |
| | 94.0 | 1.44a | 0.033 |
| | 23.4 | 1.43a | 0.123 |
| | 5.9 | 1.37ab | 0.220 |
| | 1.5 | 1.21abc | 0.006 |
| | 0.4 | 1.09acb | 0.021 |
| | 0 | 0.94c | 0.155 |
| Ribavirin (uM) applied 2 hours prior to infection of cells with WNV | 0.6 | 1.06a | 0.268 |
| | 0.5 | 1.24b | 0.430 |
| | 0.4 | 1.24b | 0.344 |
| | 0.3 | 1.11a | 0.265 |
| | 0.2 | 0.72c | 0.063 |
| | 0 | 0.57d | 0.074 |
| Interferon (0.37–1.5 units/ml) plus doses of ribavirin (uM) applied 2 hours after infection of cells with WNV | 0.50 | 1.25bc | 0.215 |
| | 0.40 | 1.56ba | 0.193 |
| | 0.30 | 1.69a | 0.354 |
| | 0.20 | 1.44ab | 0.360 |
| | 0.10 | 1.11dc | 0.223 |
| | 0.05 | 0.87d | 0.220 |
| | 0 | 0.78d | 0.168 |

*Means with the same letter within each treatment were not significantly different at $p < 0.05$ using Tukey HSD multiple comparison test.

Both ribavirin and interferon alpha-2b are active in vitro against WNV infection of bovine kidney cells. A relatively high concentration of ribavirin (400 uM), is protective or prophylactic against infection. A 400 uM concentration is equivalent to approximately 100 ug/ml: The concentration of ribavirin in human serum after 600 mg given every 6 hours is 1 ug/ml, 100-fold less than the in vitro inhibitory concentration. However, ribavirin is broadly concentrated intracellularly in vivo with subsequent phosphorylation and dephosphorylation. Thus, the relationship between in vitro inhibitory concentration, serum concentration, in vivo intracellular concentration, and ultimate in vivo antiviral effect can be predicted.

Interferon alpha-2b is both protective and therapeutic for WNV infected bovine kidney cells in vitro at relatively low concentrations, approximately 1–10 units/ml. A dose of 3 million units of interferon alpha-2b in humans provides serum levels of 10 units/ml after 8 hours, and daily doses of 3 million units yield serum levels of 20–30 units/ml, which are above the concentration required for in vitro efficacy against WNV. Although systemic administration of interferon alpha-2b produces low levels in cerebrospinal fluid and brain, beneficial effects on West Nile encephalitis may occur through suppression of viremia and/or lymphocyte activation, systemically and in the central nervous system.

Full protection of cell viability occurred when a combination of interferon alpha-2b, 1.47 units/ml, and ribavirin, 200–300 uM, was added 1.5 hours after infection of cells with WNV. Control cells infected with WNV, without addition of drug, showed loss of viability.

Ribavirin toxicities: The major toxicity of ribavirin is hemolysis due to accumulation of ribavirin triphosphate within erythrocytes leading to a decreased life span. Such accumulation occurs due to inability of erythrocytes to dephosphorylate the triphosphate. Inhibition of erythrocyte release from bone marrow occurs at high doses (30 mg/kg). Hemolysis is related to the dose and duration of therapy, and is reversible after discontinuation. A maximum of 20% reduction from baseline hematocrit occurred during effective therapy of Lassa fever with 4 gm/d for 4 days, followed by 1.5 gm/d for 6 days. Prophylactic use of ribavirin, 600 mg 4 times daily for Lassa fever contact caused a 10–12% reduction in baseline hemoglobin after 10 days. Ribavirin is teratogenic and should not be given during, or within 6 months of pregnancy. Bioavailability is increased in patients with renal dysfunction.

Interferon alpha-2b toxicities: A flu-like syndrome with fever, malaise and headache occur shortly after interferon alpha-2b administration. Longer term effects include depression and 35–40% reductions in peripheral neutrophile and platelet counts. Abnormal liver function is a relatively uncommon toxicity.

Example 2

In vivo studies are contemplated. Adult patients, with WNV encephalitis documented by positive serum or cerebrospinal fluid WNV IgM antibody, and/or positive serum WNV neutralizing antibody, will be eligible for treatment if serum creatinine clearance is above 50 ml/min.

Therapy: Patients will be treated with oral ribavirin, 1200 mg, as an initial dose, followed by 600 mg every 6 hours. Treatment with interferon alpha-2b will be given initially as an intravenous dose of 3 million units, followed by a subcutaneous injection of 3 million units after 12 hours, and then every 24 hours. Therapy with both drugs will be initiated simultaneously and continued, if tolerated, for 10 days. If patients are unable to take oral medication, the contents of ribavirin capsules, 600 mg, will be dissolved in 30 ml of sterile water and given by naso-duodenal intubation. Care will be taken to ensure that the feeding tube passes beyond the stomach to allow full absorption of ribavirin, avoiding gastric hydrolysis. Doses of ribavirin will be given 30 minutes after enteric feeding, or after an oral meal to increase absorption.

Acetaminophen, 650 mg, will be given 30 minutes prior to each dose of interferon alpha-2b. The dose of 3 million units will be reconstituted from interferon alpha-2-b (Intron A) powder for injection, and will be given intravenously (first dose) and by subcutaneous injection (subsequent doses).

Patient Examination: Patients will be examined daily throughout therapy with recording of maximum temperature, level of consciousness, orientation, mental acuity, motor and sensory function, rash, organomegaly or other abnormal findings.

Laboratory and Radiologic Studies: Prior to initiation of therapy, cerebral computerized tomography or magnetic resonance imaging, electroencephalography, lumbar puncture, complete blood count, and hepatic/renal function tests will be done. Complete blood count and hepatic/renal function tests will be repeated daily during therapy. Radiologic studies and electroericephalography will be repeated as indicated. Lumbar puncture will be repeated at the end of therapy, and at other times as indicated clinically. Therapy will be discontinued if the peripheral absolute neutrophile count falls below 1000 per $mm^3$; the peripheral platelet count falls below 50,000 per $mm^3$; hepatic enzymes increase by 3-fold; or serum creatinine increases by 2-fold and is greater than 2.0 mg/dl.

Evaluation of Treatment Outcome: The most important evaluation of treatment is patient survival, because the mortality of prior central nervous system WNV infection in New York was 11%, and higher among patients with encephalitis. This will be supplemented by an evaluation of neurologic deficits at monthly intervals for 6 months and at one year.

Example 3

In vivo studies with interferon alpha-2b: Interferon alpha-2b, as previously mentioned possesses greater activity in-vitro than ribavarin, with a potentially greater therapeutic ratio in humans. This is a pilot study of at least 10 patients designed to test tolerance of interferon alpha-2b in the treatment of central nervous system infection and its potential therapeutic effect prior to a subsequent controlled study. To initiate therapy at the earliest possible stage and before brain damage occurs, patients in this age group with any sign of central nervous system infection by WNV will be eligible.

Therapeutic Plan: Death due to WNV infection is universally due to meningitis which progress to encephalitis. Thus, therapeutic intervention should be limited to this population at risk. To initiate therapy at the earliest possible stage and before brain damage occurs, patients in this age group with any sign of central nervous system infection by WNV will be eligible. This is a pilot study of at least 10 patients designed to test tolerance of interferon alpha-2b in the treatment of central nervous system infection and its potential therapeutic effect prior to a subsequent controlled study.

Patient selection: Adult patients, with WNV meningitis or encephalitis will be treated in an open study after informed consent is obtained from the patient or appropriate surrogate. WNV infection must be documented by positive serum or cerebrospinal fluid WNV IgM antibody, and/or positive serum WNV neutralizing antibody. Because subcutaneous and intravenous interferon alpha-2b is FDA approved for treatment of hepatitis C infection, off-label use for WNV infection is allowed without further FDA or IRB approval. However, it is advisable that IRB approval be obtained for this protocol.

Therapy: Patients will be treated with an initial intravenous dose of 3 milllion units of interferon alpha-2b followed by a subcutaneous injection of 3 million units after 12 hours, and then every 24 hours. Therapy will be continued, if tolerated, for 14 days.

Acetaminophen, 650 mg, will be given 30 minutes prior to each dose of interferon alpha-2b. The dose of 3 million units will be reconstituted from interferon alpha-2b (Intron A) powder for injection, provided by Schering-Plough Corporation.

Patient Examination: Patients will be examined daily throughout therapy with recording of maximum temperature, level of consciousness, orientation, mental acuity, motor and sensory function, rash, organomegaly or other abnormal findings.

Laboratory and Radiologic Studies: Prior to initiation of therapy, cerebral computerized tomography or magnetic resonance imaging, electroencephalography, lumbar puncture, complete blood count, and hepatic/renal function tests will be done. Complete blood count and hepatic/renal function tests will be repeated daily during therapy. Radiologic studies and electroencephalography will be repeated as indicated. Lumbar puncture will be repeated at the end of therapy, and at other times as indicated clinically. Therapy will be discontinued if the peripheral absolute neutrophil count falls below 1000 cells per mm3; the peripheral platelet count falls below 50,000 per mm3; hepatic enzymes increase by 3-fold; or serum creatinine increases by 2-fold or to greater than 2.5 mg/dL. At onset of therapy, and after 7 and 14 days, 10 mL of blood will be obtained, and serum frozen at −20° C. for subsequent study of cell mediated immunity against WNV. Two mL of CSF from all lumbar punctures will be frozen for the same purpose.

Evaluation of Outcome: Unless WNV encephalitis occurs with sufficient frequency to allow a controlled, blinded study of therapy with interferon alpha-2b, only sporadic patients will be treated. Because the mortality of WNV encephalitis in North America has been approximately 20%, the most important evaluation of sporadic therapy is survival. This will be supplemented by an evaluation of neurologic deficits at monthly intervals for 6 months and at one year.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method of treating a human suffering from a meningitis, encephalitis, or meningo-encephalitis caused by a West Nile virus infection, comprising administering to the human intravenously or subcutaneously or a combination thereof an effective amount of interferon alpha-2b.

2. A method in accordance with claim 1, wherein the interferon alpha-2b is administered in an amount from about 1.5 million units to about 10 million units/day.

3. A method in accordance with claim 1, wherein the interferon alpha-2b is administered in an amount of 3 million units as an initial dose, then 3 million units every 12 to 24 hours.

4. A method in accordance with claim 1, wherein the interferon alpha-2b is administered subcutaneously to the human.

5. A method in accordance with claim 1, wherein the interferon alpba-2b is administered intravenously to the human for 14 days.

6. A method in accordance with claim 1, wherein acetaminophen is given to the an 30 minutes before the interferon alpha-2b.

7. A method of treating a human suffering from meningo-encephalitis caused by a West Nile virus infections, comprising administering to the human intravenously or subcutaneously or a combination thereof effective amount of interferon alpha-2b.

8. A method in accordance with claim 7, wherein the interferon alpha-2b is administered in an amount from about 1.5 million units to about 10 million units/day.

9. A method in accordance with claim 7, wherein the interferon alpba-2b is administered in an amount of 3 million units as an initial dose intravenously, then 3 million units every 12 to 24 hours subcutaneously.

10. A method in accordance with claim 7, wherein the interferon alpha-2b is administered subcutaneously to the human.

11. A method in accordance with claim 7, wherein the interferon alpha-2b is administered intravenously to the human for 14 days.

12. A method in accordance with claim 7, wherein acetaminophen is given to the human 30 minutes before the interferon alpha-2b.

13. A method of treating a human suffering from encephalitis caused by a West Nile virus infection, comprising administering to the human intravenously or subcutaneously or a combination thereof an effective amount of interferon alpha-2b.

14. A method in accordance with claim 13, wherein the interferon alpha-2b is administered in an amount from about 1.5 million units to about 10 million units/day.

15. A method in accordance with claim 13, wherein the interferon alpha-2b is administered in an amount of 3 million units as an initial dose intravenously, then 3 million units subcutaneously every 12 to 24 hours.

16. A method in accordance with claim 13, wherein the interferon alpha-2b is administered subcutaneously to the human.

17. A method in accordance with claim 13, wherein the interferon alpha-2b is administered intravenously to the human for 14 days.

18. A method in accordance with claim 13, wherein acetaminophen is given to the human 30 minutes before the interferon alpha-2b.

19. A method of treating a human suffering from meningitis caused by a West Nile virus infection, comprising administering to the human intravenously or subcutaneously or a combination thereof an effective amount of interferon alpha-2b.

20. A method in accordance with claim 19, wherein the interferon alpha-2b is administered in an amount of 3 million units as an initial dose intravenously, then 3 million units subcutaneously every 12 to 24 hours.

21. A method in accordance with claim 1, wherein the interferon alpha-2b is administered in an amount 3 million units as an initial dose intravenously, then 3 million units every 12 to 24 ho s subcutaneously.

* * * * *